United States Patent [19]

Fehr

[11] 4,386,220

[45] May 31, 1983

[54] POLYUNSATURATED BICYCLIC COMPOUNDS, THEIR PREPARATION AND USE OF SAME AS STARTING MATERIALS FOR PREPARING MONOUNSATURATED BICYCLIC COMPOUNDS

[75] Inventor: Charles Fehr, Geneva, Switzerland

[73] Assignee: Firmenich, SA, Switzerland

[21] Appl. No.: 366,609

[22] Filed: Apr. 8, 1982

Related U.S. Application Data

[62] Division of Ser. No. 242,013, Mar. 9, 1981.

[30] Foreign Application Priority Data

Mar. 31, 1980 [CH] Switzerland .................... 2535/80

[51] Int. Cl.$^3$ .......................................... C07C 147/02
[52] U.S. Cl. ................................................. 568/031
[58] Field of Search ........................................ 568/31

[56] References Cited

U.S. PATENT DOCUMENTS

| | | | |
|---|---|---|---|
| 3,360,577 | 12/1967 | Pickles | 585/23 |
| 3,949,011 | 4/1976 | Smirnov et al. | 585/23 |
| 4,351,977 | 9/1977 | Fehr | 585/22 |

FOREIGN PATENT DOCUMENTS

| | | | |
|---|---|---|---|
| 1873 | 5/1979 | European Pat. Off. | 568/31 |
| 37116 | 10/1981 | European Pat. Off. | 568/31 |
| 2916418 | 11/1980 | Fed. Rep. of Germany | 568/31 |

OTHER PUBLICATIONS

Dhenkne et al., "J. Chem. Soc.", (1962) p. 2346.
Mathur et al., "J. Chem. Soc." (1963) p. 3505.
Ziegler et al., "Ann. V" 512 p. 164 (1934).
MacDonald, "J. Amer. Chem. Soc.", vol. 97, p. 1264 (1975).
Chem. Abstracts, vol. 52, No. 6, (1958), "Structure and Synthesis of Muscopyridine," 4635d to 4637b.
Journal of American Chemical Society, vol. 79, pp. 5558 to 5564 (1957).

*Primary Examiner*—Werren B. Lone
*Attorney, Agent, or Firm*—Scully, Scott, Murphy & Presser

[57] ABSTRACT

New polyunsaturated compounds, their preparation and their use as starting materials for preparing monounsaturated bicyclic compounds useful as intermediates in the preparation of macrocyclic ketones.

1 Claim, No Drawings

POLYUNSATURATED BICYCLIC COMPOUNDS, THEIR PREPARATION AND USE OF SAME AS STARTING MATERIALS FOR PREPARING MONOUNSATURATED BICYCLIC COMPOUNDS

This is a division of application Ser. No. 242,013, filed Mar. 9, 1981.

SUMMARY OF THE INVENTION

The invention relates to compounds of formula

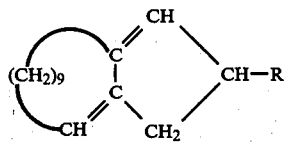

(III)

wherein symbol R represents a hydrogen atom or a methyl radical.

The invention also relates to a process for preparing said compounds (III), which comprises treating with a strong base a compound of formula

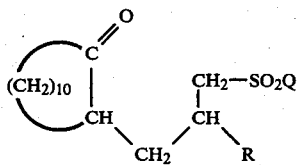

(II)

wherein symbol R is defined in formula (III) and Q represents an alkyl or an aryl radical.

The invention further relates to the use of said compounds (III) as starting materials for preparing compounds of formula

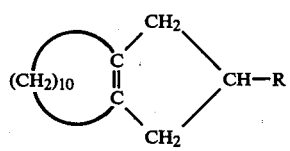

(I)

wherein symbol R is defined hereinabove, which comprises hydrogenating said compound (III) in the presence of a metal catalyst.

The invention finally relates to compounds of formula

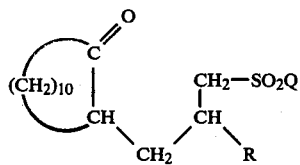

(II)

wherein symbol R represents a hydrogen atom or a methyl radical and Q represents an alkyl or an aryl radical.

BACKGROUND OF THE INVENTION

EXALTONE® and muscone, two macrocyclic ketones, are very appreciated in the art of perfumery for their elegant and tenacious musky odour. Both compounds have been known for several decades and since their discovery a variety of syntheses have been proposed and described in the scientific literature [see e.g.: J. Chem. Soc. 1964, 4154; Tetrahedron 20, 2601 (1964); Helv. Chim. Acta 50, 705 (1967) and Helv. Chim. Acta 50, 708 (1967)]. So far, however, most of the published methods could not be successfully applied to their industrial scale preparation, especially in view of their complexity or in view of the low yields achieved in the critical reaction steps.

One of the prior known syntheses [Helv. Chim. Acta 50, 705 (1967)] makes use of the compound of formula

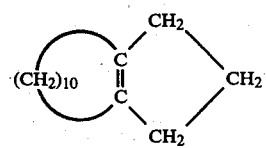

(Ia)

(R=H, in formula I) as intermediate in the synthesis of EXALTONE® (cyclopentadecanone), and of the corresponding methyl derivative of formula

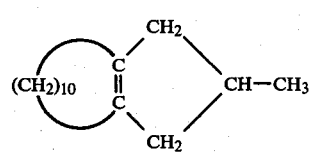

(Ib)

(R=methyl, in formula I) in the synthesis of muscone. Both intermediate compounds can be obtained from cyclododecanone by a condensation reaction and a subsequent cyclization, hydrogenation and dehydration. Due to the rather poor overall yields achieved, however, such synthetic routes have not been developed industrially.

The advantage of the invention consists in providing a new and original synthetic process for preparing the above mentioned intermediate compounds of formula (I), thus making the preparation of the desired macrocycles more convenient and industrially feasible.

PREFERRED EMBODIMENTS OF THE INVENTION

In formula (II) given above, symbol Q represents preferably a lower alkyl radical such as for instance a methyl, ethyl, propyl or butyl radical, or an aryl radical such as phenyl or p-tolyl.

According to the invention, compounds (II) are treated with a strong base, in the presence or absence of an organic solvent or mixture of organic solvents, to afford corresponding polyunsaturated bicyclic compounds (III). Formally, the reaction consists in an initial condensation reaction followed by an elimination, both steps being effected in the presence of the strong base. Condensation and subsequent elimination of water yield to an intermediate compound having formula

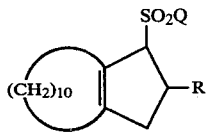

(IV)

(R and Q are defined as above) which can be, if necessary, isolated from the reaction mixture. Said intermediate compound (IV) can be further treated with a strong base to afford, after a second elimination reaction, the desired compound (III). For practical and economical reasons however, condensation and both eliminations are effected in one single reaction step.

As strong base, one can advantageously use a strong organic base such as an alkali metal alkoxide, potassium tert-butoxide, sodium methoxide or tert-pentoxide for example, or even potassium or sodium hydride or amide. In certain cases, mixtures of organic bases, sodium methoxide and potassium tert-pentoxide e.g., can be used. A strong mineral base such as potassium hydroxyde can also be used in accordance with the process of the invention.

The said base is used in excess with respect to compound (II), generally in the proportions of at least 2 to 2.5 equivalents of the base for 1 equivalent of compound (II). Depending on the nature of the base, one can also use 6 or even 10 equivalents of the base for 1 equivalent of compound (II).

As mentioned hereinabove, the treatment of compound (II) can be effected in the absence of any solvent, said compound (II) being merely heated in the presence of the selected base. For example, 2-(2-methyl-3-phenylsulfonyl-prop-1-yl)-cyclododecanone can easily be converted into the corresponding compound (III) by heating at about 160° C., in the presence of potassium tert-butoxide.

When the above treatment is effected in the presence of an organic solvent or a mixture of organic solvents, one can advantageously use an aromatic hydrocarbon, toluene or xylene e.g., an aliphatic alcohol, an ether such as tetrahydrofurane, dioxane or dimethoxy-ethane e.g., or even dimethyl-sulfoxide, ethylene-diamine or hexamethyl-phosphorous-triamide (HMPT). Depending on the nature of the solvent or mixture of solvents which is used, the reaction temperature may vary within about 60° and 160° C., preferably within about 100° and 120° C. More generally, the said temperature is of the order of the boiling temperature of the solvent or mixture of solvents used.

The polyunsaturated bicyclic compound (III) thus obtained can be then converted into the corresponding monounsaturated derivative (I), by a hydrogenation in the presence of a metal catalyst. The said hydrogenation is generally effected at atmospheric pressure, in the presence of a catalyst which is able to promote simultaneously the isomerization of an ethylenic double bond: palladium on charcoal is preferably used.

The said hydrogenation can be effected in the presence of an inert organic solvent, e.g. an aliphatic hydrocarbon, petrol ether or an aromatic hydrocarbon, benzene, toluene or xylene e.g., or an alcohol or an ether; in fact, one can use any solvent or mixture of solvents which is able to dissolve compound (III). The hydrogenation is moreover effected at a temperature generally comprised between about 20° and 120° C., preferably between about 75° and 115° C.

Compounds (II) used as starting materials in the process of the invention are novel compounds. They can be easily prepared from 2-allyl-cyclododecanone or 2-methallyl-cyclododecanone, respectively, after radical initiated addition of the appropriate thiol and subsequent oxidation. Each of the above reation steps can be carried out in accordance with the techniques known in the art: a detailed description thereof is given in the examples. The said preparation can also be illustrated as follows:

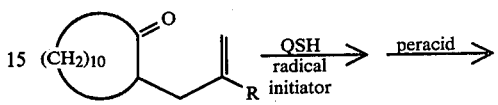

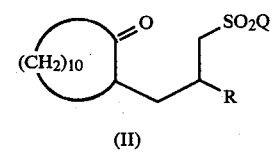

(II)

In the above reaction scheme, symbols R and Q are defined as mentioned previously.

The followings examples are deemed to illustrate the invention in a more detailed manner (temperatures in degrees centigrade).

EXAMPLE 1

Bicyclo[10.3.0]pentadeca-1,12-diene(intermediate compound not isolated)

(a) method with potassium tert-butoxide 0.728 g (2 mmole) of 2-(3-phenylsulfonyl-prop-1-yl)-cyclododecanone and 0.560 g (5 mmole) of potassium tert-butoxide in 8 ml of toluene were heated to reflux for 1 hour in a reaction vessel fitted with a water separator. After cooling to 10°, addition of water (15 ml), extraction with ether (2×15 ml), washing of the organic layer with brine (15 ml), then with water, drying over $Na_2SO_4$, evaporation and final distillation (0.02 Torr—bath temperature: 140°) there were isolated 0.340 g (83% yield) of the desired compound.

IR: 2910, 1460, 1440, 925, 915, 845 cm$^{-1}$;

NMR (90 MHz): 1.02–1.76 (14H, m); 1.95–2.68 (8H, m); 5.47 (1H, t, J=7.5 Hz); 5.72 (1H, broad s) δ ppm;

MS: M$^+$+1=205 (15), M$^+$=204 (84); m/e=175 (8), 161 (34), 148 (60), 147 (78), 134 (42), 133 (100), 119 (62), 106 (42), 105 (57), 93 (47), 91 (81), 79 (70), 67 (58).

(b) method with potassium tert-butoxide/sodium methoxide 29.0 ml of a 30% solution of sodium methoxide in methyl alcohol (0.15 mole) were added dropwise to a mixture of 36.4 g (0.10 mole) of 2-(3-phenylsulfonyl-prop-1-yl)-cyclododecanone and 200 ml of toluene, kept at reflux in a reaction vessel fitted with a water separator (addition period: ca. 1 hour). After this first addition, 14.6 g (0.13 mole) of potassium tert-butoxide were added to the reaction mixture, which was then heatedd to reflux during 4 hours. After the usual treatments of extraction and distillation, there were isolated 17.1 g (84% yield) of the desired compound.

(c) method with sodium methoxide 2.37 ml of a 30% solution of sodium methoxide in methyl alcohol (10.2 mmole) were added dropwise to a solution of 0.728 g (2.0 mmole) of 2-(3-phenylsulfonyl-prop-1-yl)-cyclododecanone in 10 ml of toluene as indicated sub letter (b). After 90 min. of heating, 0.57 ml (8.0 mmole) of dimethylsulfoxide (DMSO) were added to the reaction mixture which was then heated to reflux for 4 further hours. After extraction and distillation, there were isolated 0.310 g (76% yield) of the desired compound.

(d) method with potassium hydroxide 10.92 g (0.03 mole) of 2-(3-phenylsulfonyl-prop-1-yl)-cyclododecanone and 11.0 g (0.197 mole) of freshly powdered KOH in 40 ml of toluene were heated to reflux for 30 min. as indicated sub letter (b). After addition of 6 ml (0.085 mole) of DMSO, the reaction mixture was heated to reflux for 12 further hours, then cooled, extracted and finally distilled as indicated hereinabove to afford 5.32 g (87% yield) of the desired compound.

By adding 13.5 g (0.24 mole) of powdered KOH instead of the above mentioned 11 g, the heating period in the presence of DMSO could be reduced to 30 min.

(e) method with potassium hydroxide/ethyl alcohol 0.728 g (2 mmole) of 2-(3-phenylsulfonyl-prop-1-yl)-cyclododecanone and 0.730 g (13 mmole) of KOH in solution in 10 ml of ethyl alcohol were heated to reflux for 1 hour. After addition of 2 ml of DMSO, the reaction mixture was heated to 120° and the excess of ethyl alcohol distilled therefrom. The resulting mixture was then heated at 110° for 12 hours, then treated as indicated hereinabove to afford 0.29 g (71% yield) of the desired compound.

(f) method with sodium hydride 0.144 g (6 mmole) of NaH and 10 ml of DMSO were first heated at 80° for 30 min. Once the hydrogen evolution was terminated, 0.728 g (2 mmole) of 2-(3-phenylsulfonyl-prop-1-yl)-cyclododecanone were added to the above mixture and the resulting reaction mixture further heated at 100° for 4 hours. After the treatmments of extraction and distillation mentioned hereinabove, there were isolated 0.326 g (80% yield) of the desired compound.

(g) method with sodium hydride/ethylene-diamine 0.720 g (2 mmole) of 2-(3-phenylsulfonyl-prop-1-yl)-cyclododecanone, 0.144 g (6 mmole) of sodium hydride and 10 ml of ethylene-diamine were heated at 100° for 4 hours, then cooled, extracted and finally distilled as indicated hereinabove to afford the desired compound in a 75% yield.

(h) method with sodium tert-pentoxide 18.2 g (0.05 mole) of 2-(3-phenylsulfonyl-prop-1-yl)-cyclododecanone, 33.0 g (0.30 mole) of sodium tert-pentoxide and 100 ml of toluene were subjected to the treatments described sub letter (a). After addition of 15 ml of DMSO, heating at 110° for 4 hours and final treatments as indicated hereinabove, there were isolated 7.75 g (76% yield) of the desired compound.

EXAMPLE 2

Bicyclo[10.3.0]pentadeca-1,12-diene (intermediate compound isolated)

(i) 0.728 g (2.0 mmole) of 2-(3-phenylsulfonyl-prop-1-yl)-cyclododecanone and 0.336 g (3.0 mmole) of potassium tert-pentoxide in 8 ml of toluene were heated during 30 min. at 50°. After cooling, addition of water (15 ml), extraction with ether (2×15 ml), washing and drying as indicated hereinabove and evaporation, there were isolated 0.673 g of crude material. After crystallization in a diethyl ether/petrol ether mixture there were finally obtained 0.598 g (86% yield) of a pure compound having the following structural formula

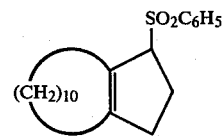

The above compound was characterized as follows:
m.p. 94°–99°
IR: 2920, 1460, 1440, 1300, 1285, 1125, 1080 cm$^{-1}$;
NMR (90 MHz): 0.95–1.95 (18H, m); 2.00–2.70 (6H, m); 4.20 (1H, d, J=7 Hz); 7.40–7.95 (5H, m) δ ppm;
MS: m/e=219 (15), 218 (8), 147 (7), 133 (7), 119 (14), 107 (17), 105 (15), 95 (35), 91 (24), 81 (21), 77 (19), 55 (19), 44 (30), 40 (100).

Analogous results were achieved by replacing in the above example potassium tert-butoxide by an equivalent amount of sodium methoxide, or by making use of 7 equivalents of powdered potassium hydroxide for 1 equivalent of starting 2-(3-phenylsulfonyl-prop-1-yl)-cyclododecanone (88% yield).

(ii) The thus prepared compound was then converted into the desired title compound by heating at 110° during 1 hour, in the presence of 1 equivalent of potassium tert-butoxide (82% yield).

2-(3-Phenylsulfonyl-prop-1-yl)-cyclododecanone used hereinabove (Examples 1 and 2) as starting material was prepared as follows: 222 g (1 mole) of 2-allyl-cyclododecanone-Helv. 54, 2889 (1971)—in admixture with 132 g (1.2 mole) of thiophenol and 3.0 g of α,α'-azoisobutyronitrile were heated at 100° for 10 hours, an additional amount of 6.0 g of α,α'-azoisobutyronitrile being added over this period, portionwise, to the reaction mixture. After dilution with an excess amount of trichloroethane and cooling in an ice-bath, 376 ml (2.6 mole) of 40% peracetic acid were progressively added to the reaction mixture, under good stirring (reaction temperature: 25°–30°). After treatment with an excess amount of an aqueous solution of NaHSO$_3$ (elimination of peroxides), a 10% solution of NaOH in water was added thereto until pH 8–9 (temperature ca. 10°). After extraction with methylene chloride (2×300 ml), successive washings with water and brine, drying over Na$_2$SO$_4$, evaporation and crystallization of the crude residue in a CH$_2$Cl$_2$/diethyl ether/petrol ether mixture, there were finally isolated 332 g (91% yield) of the desired compound, m.p. 97°–102°.
IR: 2950, 1700, 1465, 1445, 1300, 1145, 1080, 790 cm$^{-1}$;
NMR (60 MHz): 1.00–2.00 (22H, m); 2.30–2.75 (3H, m); 2.90–3.25 (2H, m); 7.50–8.02 (5H, m) δ ppm;
MS: M$^+$=364 (30); m/e=254 (8), 240 (15), 223 (12), 143 (32), 98 (41), 55 (100), 41 (59).

EXAMPLE 3

14-Methyl-bicyclo[10.3.0]pentadeca-1,12-diene (intermediate compound not isolated)

11.35 g (0.03 mole) of 2-(2-methyl-3-phenylsulfonyl-prop-1-yl)-cyclododecanone and 11.0 g (0.197 mole) of powdered KOH in 30 ml of toluene were first heated to reflux during 30 min., in a reaction vessel fitted with a water separator. After addition of 6 ml of DMSO, the reaction mixture was further heated at 110°, for 12 hours. After the treatments of extraction, washing, drying and distillation (0.05 Torr—bath temperature: 150°) described in Example 1, there were isolated 5.61 g (86% yield) of the desired compound.

IR: 2920, 1460, 1440, 835 cm$^{-1}$;

NMR (90 MHz): 1.00 (3H, d, J=7 Hz); 1.08-1.73 (14H, m); 1.80-2.40 (5H, m); 2.55-2.91 (2H, m); 5.40 (1H, t, J=7.5 Hz); 5.60 (1H, broad s) δ ppm;

MS: M$^+$=218 (93); m/e=203 (80), 175 (30), 161 (70), 147 (100), 133 (92), 112 (68), 107 (60), 106 (44), 105 (68), 94 (55), 93 (72), 91 (75), 79 (55), 67 (32), 55 (38).

EXAMPLE 4

14-Methyl-bicyclo[10.3.0]pentadec-1,12-diene (intermediate compound isolated)

(i) 0.58 ml of a 30% solution of sodium methoxide in methyl alcohol (3 mmole) were added to 0.756 g (2 mmole) of 2-(2-methyl-3-phenylsulfonyl-prop-1-yl)-cyclododecanone in 8 ml of toluene and the resulting mixture was heated to reflux for 1 hour as indicated in Example 3. After the above treatments of extraction and distillation (0.01 Torr—bath temperature: 200°), there were isolated 0.627 g (87% yield) of a compound having the formula

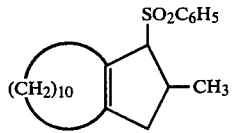

The above compound was characterized as follows:
IR: 2945, 1470, 1445, 1300, 1140, 1080 cm$^{-1}$;

NMR (90 MHz): 0.90-1.80 (22H, m); 2.20-3.00 (4H, m); 3.78 (1H, broad s); 7.35-7.96 (5H, m) δ ppm;

MS: m/e=220 (9), 219 (48), 149 (9), 147 (12), 133 (13), 123 (13), 119 (24), 109 (22), 107 (33), 105 (28), 95 (38), 94 (71), 93 (30), 91 (45), 81 (62), 79 (29), 69 (44), 67 (31), 57 (36), 55 (50), 44 (44), 43 (40), 41 (56), 40 (100).

(ii) The thus prepared compound was then converted into the desired title compound by heating at 110° in toluene, in the presence of 1 equivalent of potassium tert-butoxide and by subsequent treating the reaction mixture as discharged in Example 3.

2-(2-Methyl-3-phenylsulfonyl-prop-1-yl)-cyclododecanone used hereinabove (Examples 3 and 4) as starting material was prepared as follows: 235 g (1 mole) of 2-methallyl-cyclododecanone—Chem. Comm. 1976, 1021—in admixture with 132 g (1.2 mole) of thiophenol and 3.0 g (0.018 mole) of α,α'-azoisobutyronitrile were heated at 115° for 32 hours and subsequently subjected to oxidation in accordance with the method described in Example 2 for 2-(3-phenylsulfonyl-prop-1-yl)-cyclododecanone to afford, after the above mentioned treatments of extraction and purification, 325 g (86% yield) of the desired compound, m.p. 98°-103°.

IR: 2950, 1705, 1470, 1450, 1305, 1145, 1085 cm$^{-1}$;

NMR (60 MHz): 0.90-2.20 (24H, m); 2.30-2.75 (3H, m); 3.00 (2H, d, J=5 Hz); 7.50-8.02 (5H, m) δ ppm;

MS: M$^+$=378 (14); m/e=255 (20), 237 (22), 143 (15), 98 (24), 95 (32), 83 (52), 81 (49), 77 (50), 69 (36), 67 (32), 55 (100), 43 (41), 41 (83).

EXAMPLE 5

Bicyclo[10.3.0]pentadec-1(12)-ene 6.06 g of bicyclo[10.3.0]pentadec-1,12-diene—crude material; see Example 1—in 40 ml of toluene were hydrogenated at 100°, under atmospheric pressure, in the presence of 0.6 g of 10% palladium on charcoal. After 60 min. of hydrogenation, the reaction mixture was cooled, filtered on CELITE and finally distilled (0.02 Torr—bath temperature: 140°) to afford 5.2 g (84% yield) of the desired title compound having a purity of 93% according to vapour phase chromatography analysis (CARBOWAX 10%—1.6 m—140°). The compound thus prepared was found identical with a sample prepared according to J. Amer. Chem. Soc. 79, 5558 (1957).

Analogous results were obtained by subjecting the starting material to hydrogenation at 115° in xylene or at 75° in ethyl alcohol.

EXAMPLE 6

14-Methyl-bicyclo[10.3.0]pentadec-1(12)-ene 6.48 g of 14-methyl-bicyclo[10.3.0]pentadeca-1,12-diene—crude material; see Example 3—in 40 ml of toluene were hydrogenated in the presence of 0.65 g of 10% palladium on charcoal as indicated in Example 5. After the above treatments of filtration and distillation, there were obtained 5.69 g (86% yield) of the desired title compound having a purity of 95% according to the vapour phase chromatography analysis (CARBOWAX 10%—1.6 m—140°). The compound thus prepared was found identical with a sample prepared according to Chem. Abstr. 70, 88108 v (1970).

EXAMPLE 7

14-Methyl-bicyclo[10.3.0]pentadeca-1,12-diene 0.756 g (2 mmole) of 2-(2-methyl-3-phenylsulfonyl-prop-1-yl)-cyclododecanone and 0.672 g (6 mmole) of potassium tert-butoxide were progressively heated to 160° under 0.02 Torr and the formed title compound directly distilled from the reaction mixture. There were thus isolated 0.216 g (50% yield) of the desired compound.

EXAMPLE 8

Bicyclo[10.3.0]pentadeca-1,12-diene 10 g (0.029 mole) of 2-(3-n-butylsulfonyl-prop-1-yl)-cyclododecanone in 40 ml of toluene were heated to reflux for 30 min. in the presence of powdered KOH, in accordance with the process of Example 1, letter (b). After addition of 6 ml of DMSO, heating to reflux for 12 further hours and usual treatments of extraction and distillation as previously described, the desired title compound was isolated in a 84% yield.

2-(3-n-Butylsulfonyl-prop-1-yl)-cyclododecanone used hereinabove as starting material was prepared from 2-allyl-cyclododecanone and n-butylthiol by heating it at 95° for 10 hours in the presence of α,α'-azoisobutyronitrile and subsequently of oxidizing and purifying it in accordance with the method given in Example 2.

Yield 88%; m.p. 91.5°.

IR: 2950, 1700, 1470, 1300, 1140 cm$^{-1}$;

NMR: 0.85-2.10 (29H, m); 2.25-3.15 (7H, m) δ ppm;

MS: M$^+$=344 (5); m/e=261 (4), 233 (9), 220 (20), 123 (48), 98 (49), 83 (40), 69 (60), 55 (100), 41 (83).

What I claim is:

1. A compound having the formula

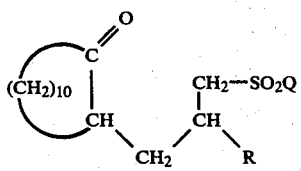
(II)
wherein symbol R represents a hydrogen atom or a methyl radical and Q represents an alkyl or an aryl radical.
* * * * *

UNITED STATES PATENT AND TRADEMARK OFFICE
CERTIFICATE OF CORRECTION

PATENT NO. : 4,386,220
DATED : August 3, 1983
INVENTOR(S) : Charles Fehr

It is certified that error appears in the above-identified patent and that said Letters Patent are hereby corrected as shown below:

Column 4, line 63: "heatedd" should read as --heated--;

Column 5, line 38: "treatmments" should read as --treatments--;

Column 6, line 33: "Helv. 54" should read as --Helv. 54--;

Column 7, line 4: "$cm^1$" should read as --$cm^{-1}$--;

Column 7, line 44: "discharged" should read --described--.

Signed and Sealed this

Twenty-seventh Day of December 1983

[SEAL]

Attest:

GERALD J. MOSSINGHOFF

Attesting Officer   Commissioner of Patents and Trademarks